(12) United States Patent
Shawer et al.

(10) Patent No.: US 8,518,935 B2
(45) Date of Patent: Aug. 27, 2013

(54) AMORPHOUS BESIFLOXACIN SOLID

(75) Inventors: Mohannad Shawer, Webster, NY (US); Eric Phillips, Ontario, NY (US); Harry M. King, Jr., Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 225 days.

(21) Appl. No.: 12/956,009

(22) Filed: Nov. 30, 2010

(65) Prior Publication Data

US 2011/0144329 A1    Jun. 16, 2011

Related U.S. Application Data

(60) Provisional application No. 61/285,659, filed on Dec. 11, 2009.

(51) Int. Cl.
  *A61K 31/55*    (2006.01)
  *A61P 31/04*    (2006.01)
  *C07D 401/04*   (2006.01)

(52) U.S. Cl.
  USPC ..................... 514/217.07; 540/597

(58) Field of Classification Search
  USPC ..................... 514/217.07; 540/597
  See application file for complete search history.

(56) References Cited

U.S. PATENT DOCUMENTS 5,447,926 A    9/1995    Konno et al.

FOREIGN PATENT DOCUMENTS

JP    61-225181    10/1986
JP    64-090183    4/1989

OTHER PUBLICATIONS

Martindale, The Complete Drug Reference, 34th ed., 2005, pp. 1411-1416.
Remington, The Science and Practice of Pharmacy, 21st ed., 2005, p. 291.
Remington, Coarse Dispersions, Chapter 22, 2006, pp. 319-337.
Tyle, Iontophoretic Devices for Drug Delivery, Pharm. Res., 1986, pp. 318-326, vol. 3, No. 6.

*Primary Examiner* — Brenda Coleman
(74) *Attorney, Agent, or Firm* — Toan P. Vo

(57) ABSTRACT

Amorphous solid-state form of (R)-(+)-7-(3-amino-2,3,4,5,6,7-hexahydro-1H-azepin-1-yl)-1,4-dihydro-4-oxoquinoline-3-carboxylic acid is characterized by at least one of: (a) an X-ray powder diffraction ("XRPD") spectrum that comprises peaks at $2\theta$ angles of 6.9-7.1, 9.4, 10.6-10.7, and 13.4-13.7°±0.2°, and a diffuse halo pattern at 11-30°; and (b) a DSC (differential scanning calorimetry) melting peak at about 267-272° C. The amorphous solid is prepared by rapid precipitation from a saturated or supersaturated solution of besifloxacin free base in a solvent comprising at least benzyl alcohol.

14 Claims, 8 Drawing Sheets

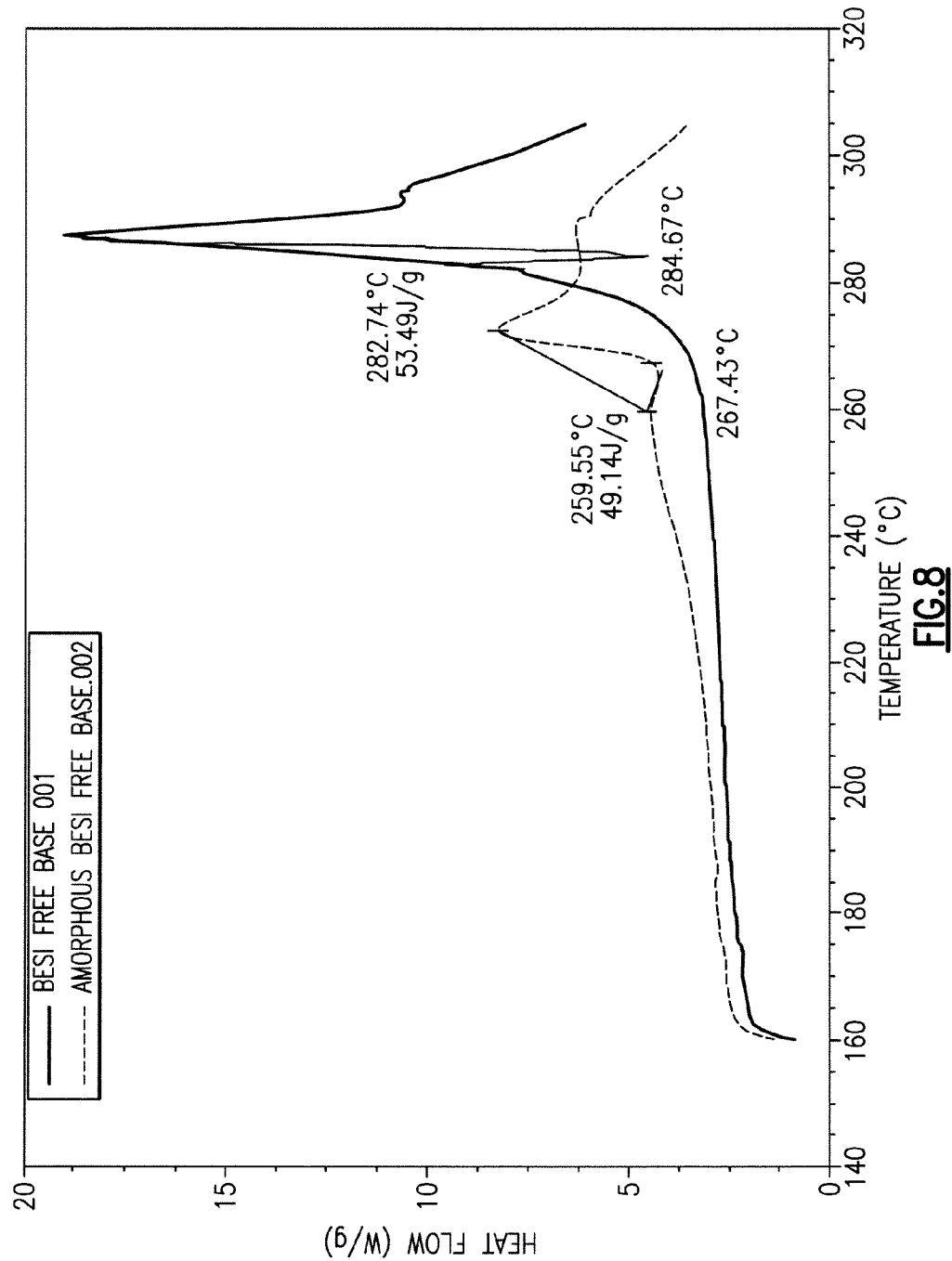

AMORPHOUS BESIFLOXACIN SOLID

CROSS REFERENCE

This application claims the benefit of Provisional Patent Application No. 61/285,659 filed Dec. 11, 2009, which is incorporated by reference herein

BACKGROUND OF THE INVENTION

The present invention relates to amorphous solid of besifloxacin ((R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid), processes of preparing, processes of using, and compositions comprising such solid.

Synthetic antimicrobial agents such as nalidixic acid, piromidic acid, and the like are known as drugs for curing infectious diseases caused by Gram negative microorganisms. They exhibit, however, only deficient effects on intractable diseases such as pseudomoniasis and the like.

On the other hand, quinolone carboxylic acid derivatives substituted with a fluorine atom at 6 position, such as norfloxacin, ofloxacin, and ciprofloxacin, or quinolone carboxylic acid derivatives substituted with a chlorine atom at 8 position have been developed (Japanese Patent Laid-open (ko-kai) Nos. 225181/1986, 90183/1984) and clinically used because of their strong antimicrobial activity.

These conventional synthetic antimicrobial agents had defects of insufficient absorptivity in a living body, providing only low bioavailability, and of a low antimicrobial activity against Gram positive microorganisms.

Therefore, development of antimicrobial agents having strong antimicrobial activity against both Gram positive and Gram negative microorganisms, including resistant bacteria, and superior absorptivity in living bodies has been desired. Recently, besifloxacin ((R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid), a new fluoroquinolone carboxylic acid, was developed and approved for the treatment of bacterial conjunctivitis. Besifloxacin offers some advantages over prior fluoroquinolones against certain types of bacteria.

Active pharmaceutical agents ("APIs") are often organic molecules, which can exist in different organic solid-state forms depending on their processes of manufacture. Such different solid-state forms can have practical influence on pharmaceutical compositions comprising these APIs, such as their processability, physical, chemical, and/or pharmacokinetic properties, stability, etc.

Therefore, it is desirable to provide a solid-state form of besifloxacin that has advantageous properties. In particular, it is very desirable to provide a solid-state form of besifloxacin that has advantageous properties for the manufacture of novel anti-infective pharmaceutical compositions.

SUMMARY

In general, the present invention provides an amorphous solid state of besifloxacin (or in other words, besifloxacin in an amorphous solid state), which has a chemical name of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid. Besifloxacin is presented by Formula I.

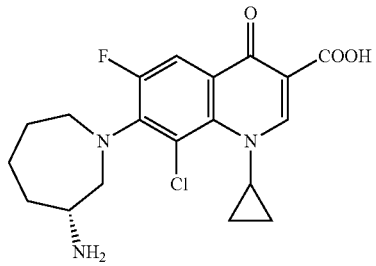

(I)

In one aspect, the present invention provides an amorphous solid-state form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°.

In another aspect, the present invention provides an amorphous solid-state form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by a DSC (differential scanning calorimetry) melting peak at about 267-272° C.

In still another aspect, the present invention provides an amorphous solid-state form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°, and a DSC (differential scanning calorimetry) melting peak at about 267-272° C.

Other features and advantages of the present invention will become apparent from the following detailed description and claims and the appended drawings.

BRIEF DESCRIPTION OF THE DRAWINGS

FIG. 8 compare DSC scans of besifloxacin free base starting material of Example 1 and amorphous besifloxacin free base of Example 2.

DETAILED DESCRIPTION OF THE INVENTION

Figure 1:
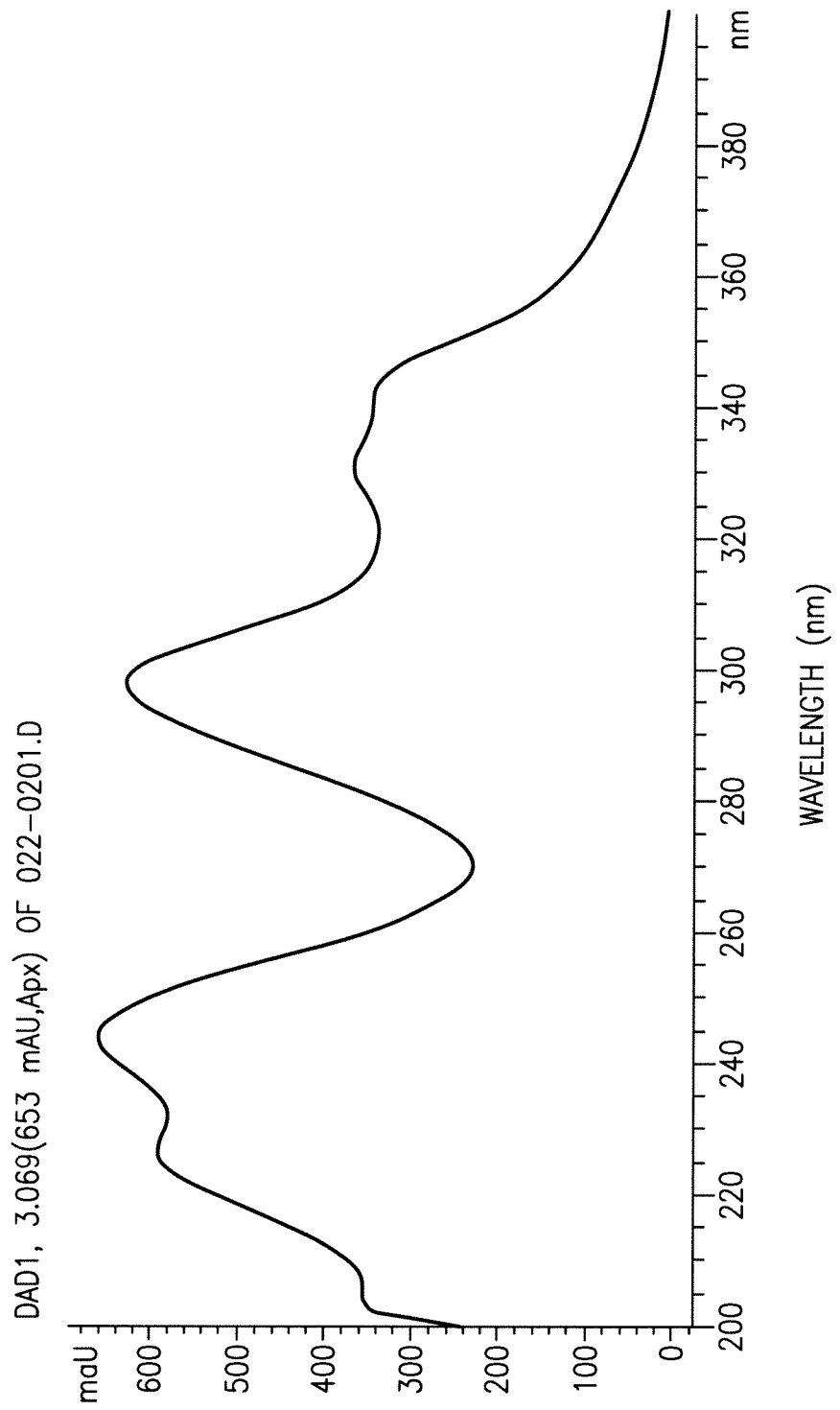
FIG. 1 shows a UV absorption spectrum of besifloxacin free base starting material of Example 1.

As used herein, the term "control" also includes reduction, alleviation, amelioration, and prevention.

In general, the present invention provides an amorphous solid state of besifloxacin, which has a chemical name of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid. Besifloxacin is presented by Formula I.

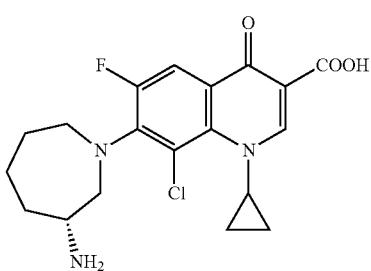

(I)

Throughout the present disclosure and claims, (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid is also referred to alternatively as besifloxacin.

Synthesis of the molecule (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid is disclosed in U.S. Pat. No. 5,447,926, which is incorporated herein by reference in its entirety.

Amorphous Besifloxacin Solid

The present inventor unexpectedly and surprisingly discovered that besifloxacin free base could be prepared in amorphous solid form, which can offer certain practical advantages, such as a higher intrinsic solubility in water (for example, at room temperature) than besifloxacin crystalline solid.

In one embodiment, such higher aqueous solubility of amorphous besifloxacin free base can enable the preparation of a besifloxacin solution at higher concentration of dissolved besifloxacin, offering a better bioavailability of the active compound at the target tissue.

An amorphous besifloxacin solid of the present invention can be prepared by a process comprising rapid precipitation of besifloxacin free base from a besifloxacin-saturated solution. The phrase "rapid precipitation" herein means a condition for initiating the precipitation of amorphous besifloxacin solid is achieved in a period of less than 10 minutes (or less than about 10 minutes). Alternatively, such condition is achieved in a period of less than 5 minutes (or less than about 5 minutes); preferably, less than 2 minutes (or less than about 2 minutes).

In one embodiment, an amorphous besifloxacin solid of the present invention can be prepared by a process comprising rapid precipitation of besifloxacin free base from a besifloxacin-saturated solution by reducing the temperature of said besifloxacin-saturated solution to a lower temperature. Thus, in one embodiment, a process for preparing an amorphous besifloxacin solid comprises: (a) preparing a saturated solution of besifloxacin free base in benzyl alcohol at a first temperature; and (b) reducing the temperature of the solution to a second temperature, whereby said amorphous besifloxacin solid is formed.

The first temperature can be in the range from about 60 to about 200° C. Alternatively, the first temperature can be in the range from about 80 to about 180° C. (or from about 80 to about 160° C., or from about 80 to about 140° C., or from about 80 to about 120° C., or from about 100 to about 140° C., or from about 100 to about 130° C.).

The second temperature can be in the range from about −15 to about 50° C. Alternatively, the first temperature can be in the range from about −10 to about 50° C. (or from about −5 to about 50° C., or from about 0 to about 40° C., or from about 0 to about 25° C., or from about −10 to about 25° C., or from about −10 to about 10° C.).

In one embodiment, said second temperature is attained after 10 minutes (or after about 10 minutes). Alternatively, said second temperature is attained after 5 minutes (or after about 5 minutes); preferably, after 2 minutes (or after about 2 minutes).

In another embodiment, the process further comprising keeping the solution at said second temperature to obtain said amorphous besifloxacin solid.

The process can further comprise recovering said amorphous besifloxacin solid from said solution.

In another embodiment, the process further comprises removing residual benzyl alcohol solvent from said amorphous besifloxacin solid.

In still another embodiment, a process for preparing an amorphous besifloxacin solid comprises: (a) preparing a first saturated solution of besifloxacin free base in benzyl alcohol at a first temperature; (b) reducing the temperature of the solution to a second temperature, which is lower than said first temperature; (c) preparing a second saturated solution of besifloxacin free base in a second organic solvent other than benzyl alcohol at said second temperature, said second organic solvent being soluble in benzyl alcohol at said second temperature; and (d) adding an amount of said second saturated solution to said first saturated solution at said second temperature, whereby said amorphous besifloxacin solid is formed.

The process can further comprise repeating step (d) one or more times. In one embodiment, the time interval between two successive repetitions of step (d) is about 24 hours (or alternatively, about 12 hours or about 6 hours).

The process can further comprise recovering said amorphous besifloxacin solid from a solution resulting from said adding second solution to said first solution.

In another embodiment, the process further comprises removing residual benzyl alcohol solvent and said second organic solvent from said amorphous besifloxacin solid.

In a further embodiment, said second organic solvent comprises methanol.

EXAMPLE 1

Preparation of Besifloxacin Free Base Solid

Besifloxacin free base was prepared from besifloxacin hydrochloride addition salt.

An amount of about 5 g of besifloxacin HCl (HCl addition salt of besifloxacin made, for example, by the method of U.S. Pat. No. 5,447,926; which is incorporated herein by reference in its entirety) was added to about 750 ml of water. The besifloxacin HCl was allowed to dissolve in said water. Twenty milliliters of 1N NaOH solution were added slowly to the besifloxacin aqueous solution while stirring (final pH 10.2). Besifloxacin free base started to precipitate. Eight milliliters of 1N HCl solution were added slowly while stirring (final pH of 9.7). The resulting mixture was allowed to mix for 2 hours while besifloxacin free base continued to precipitate. At the end of 2 hours, the precipitated besifloxacin free base was filtered through a Millipore type RA 1.2 μm filter. The besifloxacin free base thus collected was dried in a vacuum oven at room temperature. 4.35 g of besifloxacin free base was recovered.

EXAMPLE 2

Preparation of Amorphous Besifloxacin Free Base by Precipitation from Solution of Benzyl Alcohol An amount of 200 mg of besifloxacin free base prepared as described in Example 1 was added to 10 ml of benzyl alcohol in a glass scintillator vial. The vial containing the mixture was placed in a heated oil bath at 120° C. for 20 minutes. Most of the besifloxacin free base was dissolved. The mixture was filtered through a 0.22 μm filter while it was still hot. The filtrate was left undisturbed to precipitate at room temperature. The precipitate was filtered through another 0.22 μm filter and dried under vacuum at room temperature to yield amorphous besifloxacin free base (Lot 2829-MS-64-A).

EXAMPLE 3

Preparation of Amorphous Besifloxacin Free Base by Evaporation of Super-Saturated Solution of Benzyl Alcohol An amount of 787.8 mg of besifloxacin free base prepared as described in Example 1 was added to 58 ml of benzyl alcohol in a glass vial, which was kept at 60° C. overnight. The solution was then filtered and allowed to reach room temperature. No precipitation was observed.

A saturated solution of the same besifloxacin free base in methanol was prepared.

To a 10 ml aliquot of the solution of the besifloxacin-in-benzyl alcohol solution was added a volume of 70 ml of the besifloxacin-in-methanol solution. The resulting solution was allowed to evaporate for at least 8 hours. These steps were repeated 4 times over several days.

A volume of 2 ml of the final solution was evaporated in a round bottom flask at 50° C. under vacuum and amorphous besifloxacin free base was recovered (Lot #2892EP198-48).

Characterization of Amorphous Besifloxacin Prepared According to the Present Invention In order to confirm the identity of the amorphous besifloxacin free base material prepared herein, we compared the UV absorbance of the besifloxacin free base prepared according to Example 1 to the new amorphous besifloxacin free base prepared according to Example 2 using the same HPLC method. (column: Phenomenex Luna 3μ C18(2) 100A, 150× 4.60 mm 3 μm C18 flow rate: 1 ml/minute; buffer: 65% $H_2O$-0.1% trifluoroacetic acid: 35% acetonitrile-0.1% trifluoroacetic acid; detector: DAD at 298 nm; run time: 5 minutes).

Figure 2:
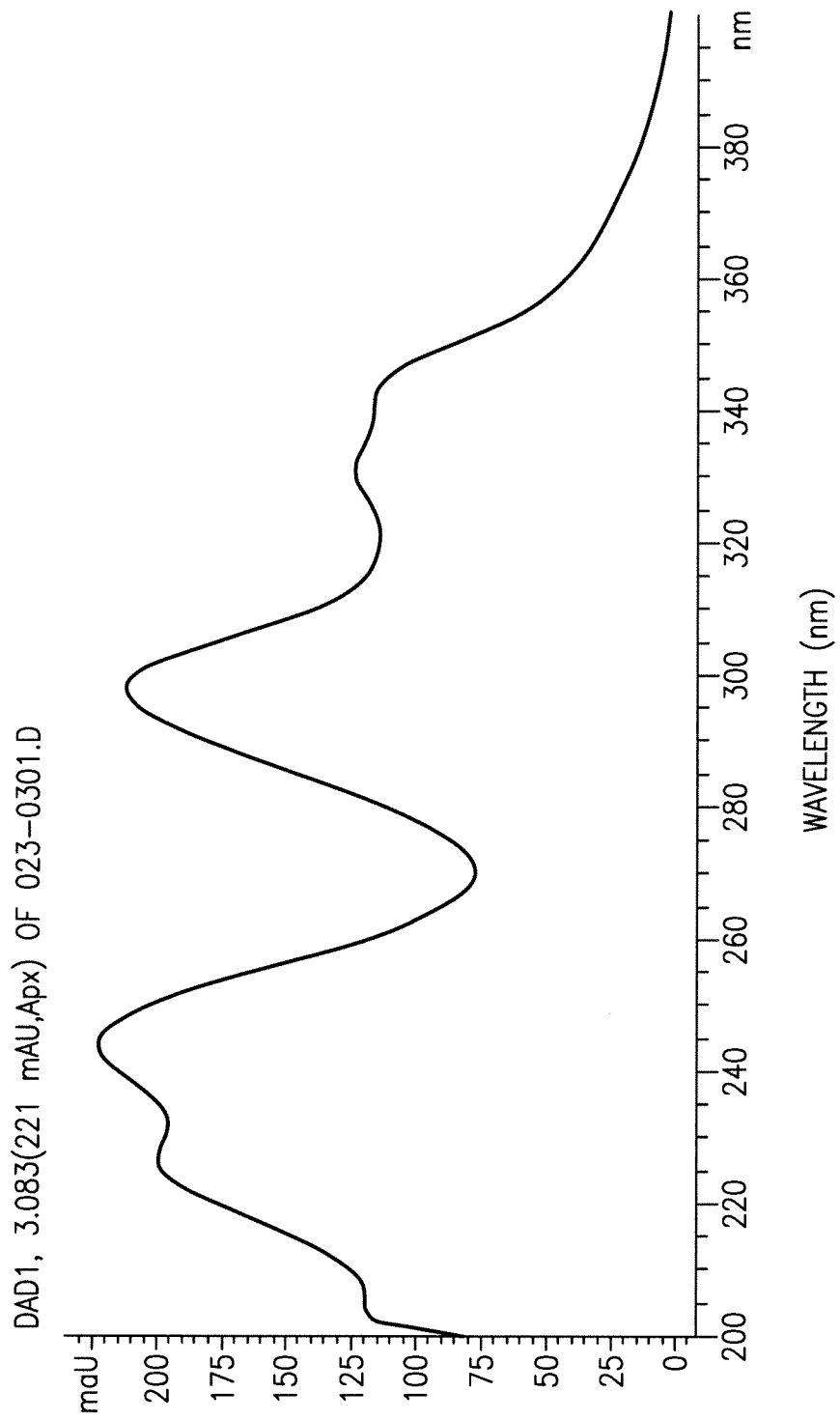
FIG. 2 shows a UV absorption spectrum of the amorphous besifloxacin free base of Example 2.

Retention time was confirmed to be the same for both samples and the unique besifloxacin free base UV absorbance spectrum at various wavelengths was identical in both samples (See FIGS. 1 and 2). Due to the processing of the amorphous samples; residual solvent (benzyl alcohol) was detected.

Characterization by Infrared Spectroscopy

Figure 3:
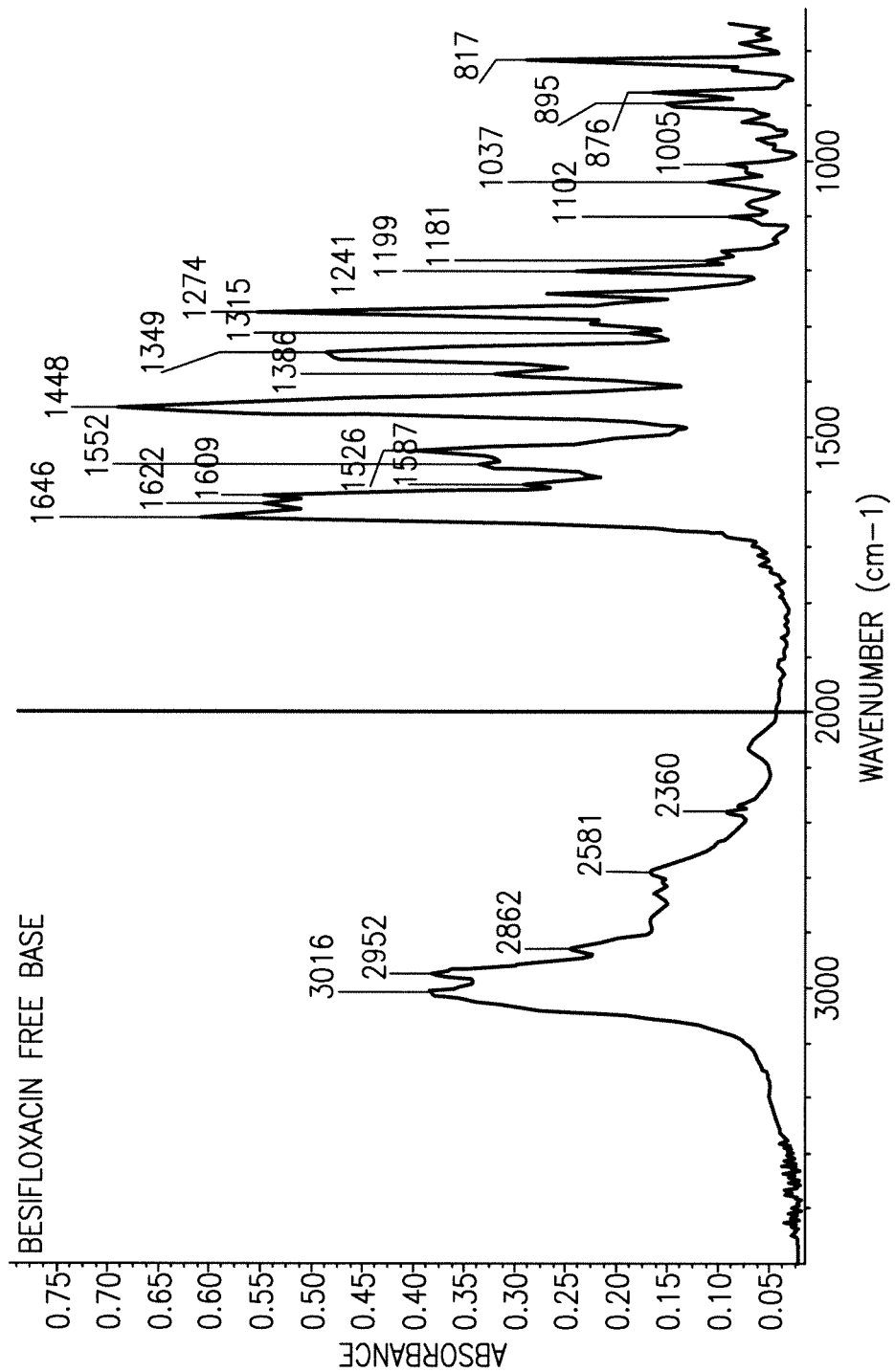
FIG. 3 shows an IR spectrum of free base starting material of Example 1.
Figure 4:
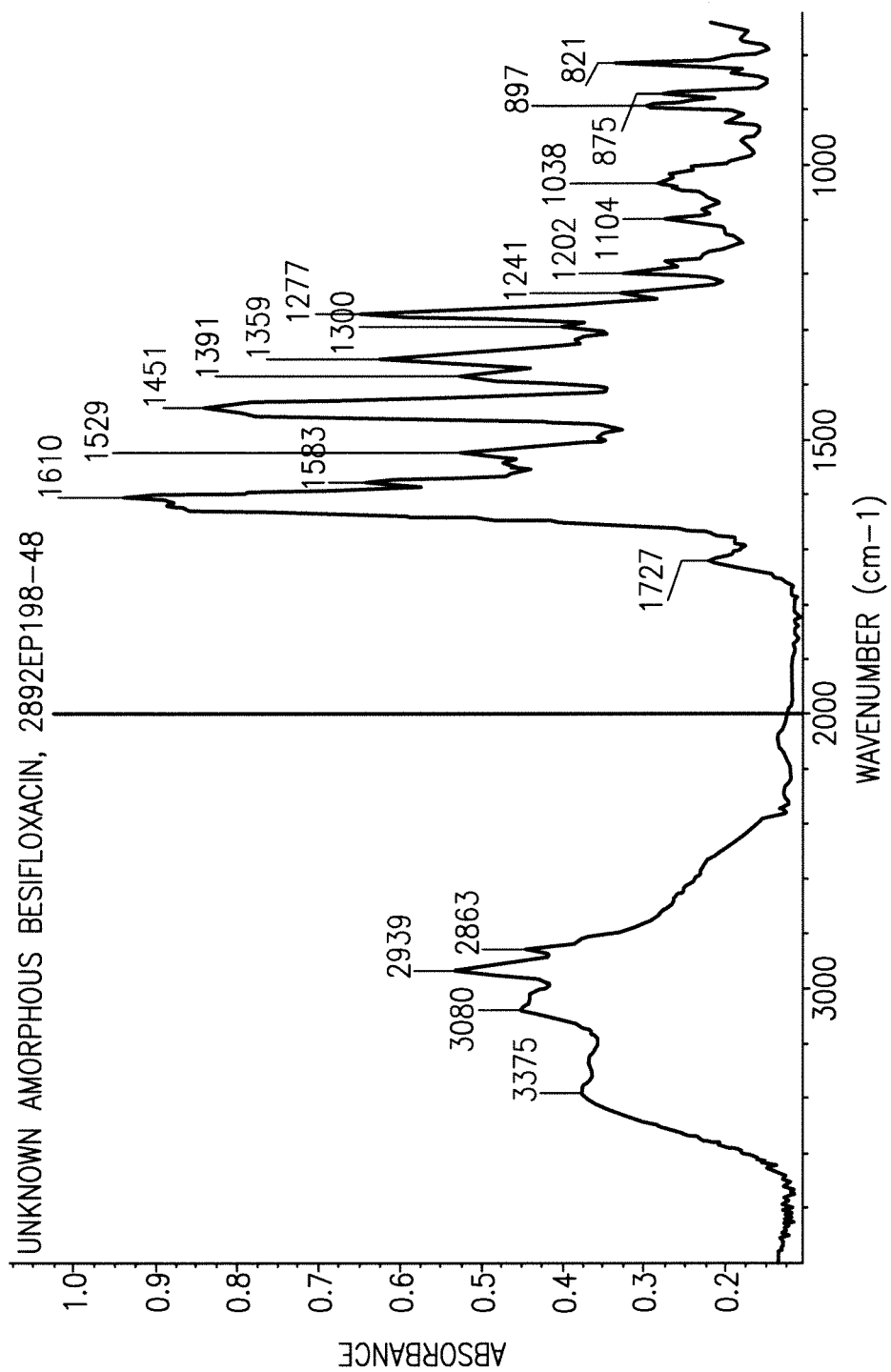
FIG. 4 shows an IR spectrum of amorphous besifloxacin free base of Example 3.
Figure 5:
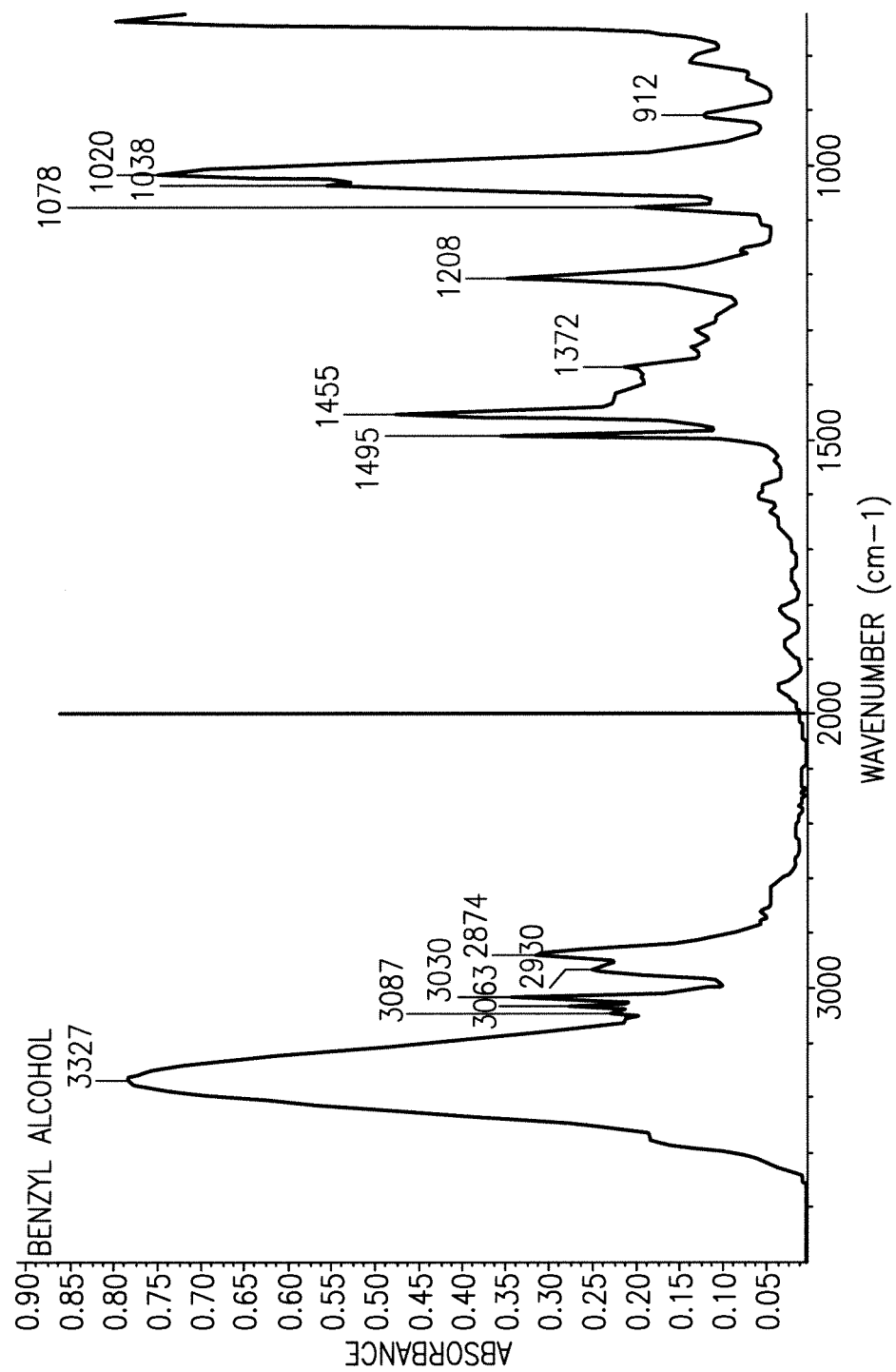
FIG. 5 shows an IR spectrum of the benzyl alcohol used to prepare the novel amorphous besifloxacin free base.

Infrared spectra of besifloxacin free base starting material obtained according Example 1 and the amorphous besifloxacin free base of Example 3 were compared (FIGS. 3 and 4). The newly discovered amorphous form has substantially the same peaks as the besifloxacin free base starting material of Example 1, with slight shifts in the some of the peaks. The substantially same peaks of FIGS. 3 and 4 indicate that that the new amorphous material has the same chemical identity as the starting besifloxacin free base. The shifts observed in some of the peaks are another indication to the physical changes that maybe associated with the new physical form of besifloxacin free base. Due to the presence of residual solvent (benzyl alcohol) during processing of the amorphous form, a control sample of this solvent was run to confirm that the new peaks observed in the amorphous samples were due in fact to the presence of residual solvent in the sample and not due to structural changes (FIG. 5).

Characterization by XRD (X Ray Diffraction) Spectroscopy

Powder X-ray diffraction patterns were collected using a Rigaku MiniFlex desktop X-ray diffractometer (serial #CD016610). The MiniFlex has a vertical-oriented goniometer (150 mm radius) and a Copper sealed X-ray tube operated at 30 kV/15 mA with a 6° take-off angle. The instrument uses a variable (theta compensating) divergence slit system and a Nickel Kβ. filter. A scintillation counter is used as the detector. An ASC-6 sample changer/spinner is used to spin the sample during diffraction pattern measurement. Jade version 7.5 software from Materials Data, Inc. was used for pattern evaluation and generation of figures.

The besifloxacin free base sample powder, which was tested was placed near the center of a circular "zero background" sample holder. In an effort to achieve a flat powder bed of the appropriate height the powder was gently compressed in a downward motion with a glass slide covered with weigh paper. Samples were scanned over a region of 2-40° 2θ at 0.5° degree/minute with a with a step size of 0.02°/step while spun.

Figure 6:
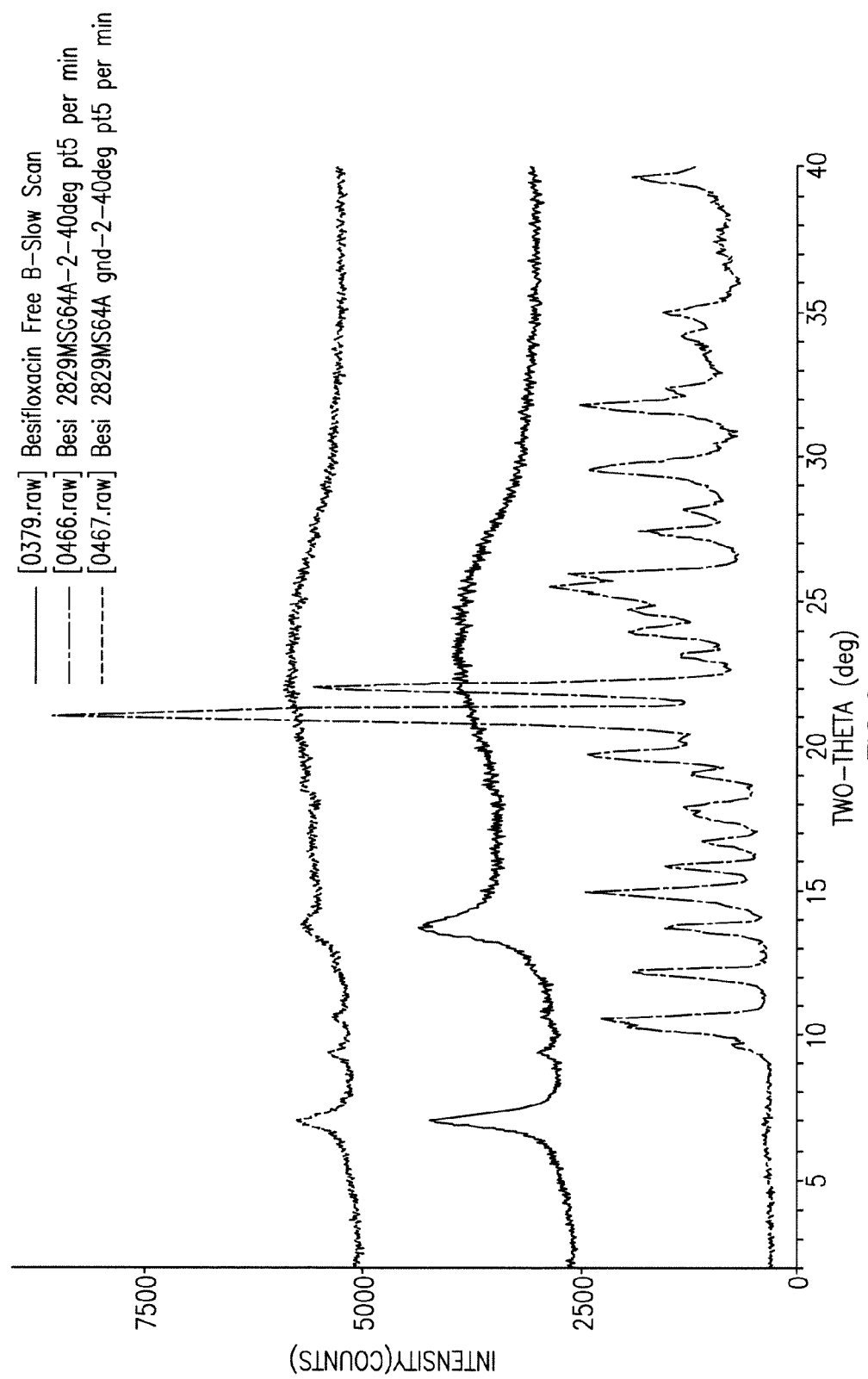
FIG. 6 compares XRD spectra of besifloxacin free base starting material of Example 1, amorphous besifloxacin free base of Example 2, and the same that has been micronized.
Figure 7:
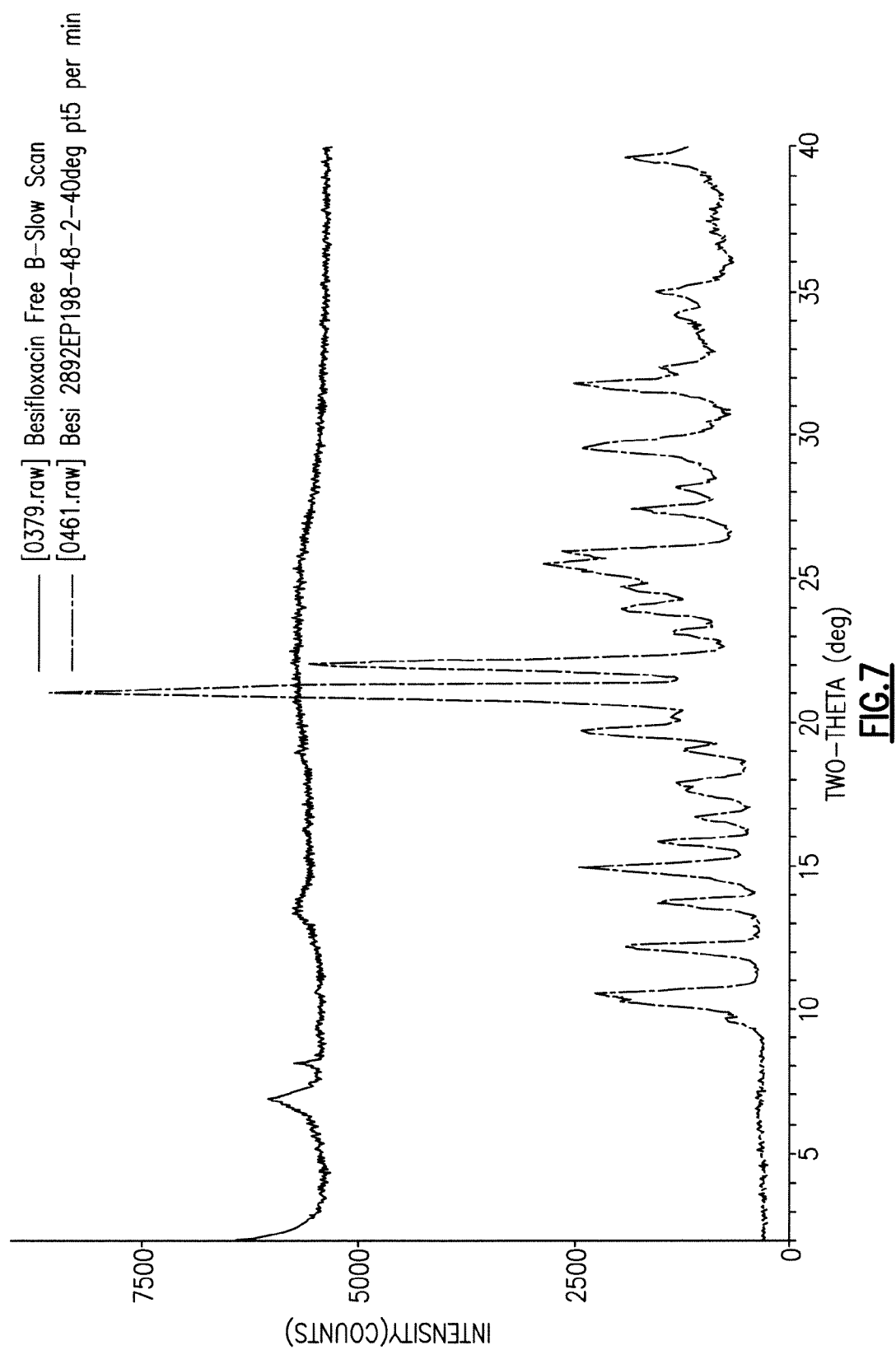
FIG. 7 compares XRD spectra of besifloxacin free base starting material of Example 1 and amorphous besifloxacin free base of Example 3.

X-ray diffraction (XRD) patterns are obtained from the interaction of monochromatic X-ray radiation with the sample powder. The atoms in a crystalline powder form a periodic array of coherent scatters. Diffraction from different planes of atoms within this crystalline material produce a pattern of sharp diffraction peaks containing information about the atomic arrangement within the crystal. In contrast to the crystalline powder, the atoms in an amorphous powder have only short-range order which produces very broad diffraction peaks or halos when interacting with the monochromatic x-ray radiation. As observed in FIGS. 6 and 7, amorphous besifloxacin free base solids prepared according to Examples 2 and 3 show similar broad diffraction peaks and the disappearance of the sharp peaks present in the spectrum of the besifloxacin free base starting material of Example 1, which indicates that the starting material is a crystalline material.

Characterization by Differential Scanning Calorimetry ("DSC")

Equipment used: TA instrument Q series DSC (Software: Universal V4.5A

Sample: (0.47 mg sample of besifloxacin free base starting material (lot #2892EP170B, prepared according to Example 1) and 0.42 mg sample of the novel amorphous besifloxacin free base (Lot #2892MS64A) were placed in t-zero Al pan and lead). The sample was equilibrated at 160° C. for 1 minute. Then the temperature was ramped at 20° C./minute from 160 to 310° C.

A comparison of the melting/decomposition of the crystalline besifloxacin free base starting material (Example 1) to that of the amorphous form (Example 2) shows significant drop in the melting/decomposition temperature for the amorphous form. This provides further evidence for the different structure of the amorphous solid in comparison to the starting material. See FIG. 8. The higher melting/decomposition temperature of the starting material indicates that it generally has a more ordered structure than the new amorphous solid. The estimated melting/decomposition temperature of the besifloxacin free base staring material is 285° C. while that of the new amorphous form it about 267° C. (when measured at a heat rate of 20° C./minute).

Conclusion

The present invention provides a new amorphous besifloxacin free base solid that heretofore has not been realized.

The solubility of besifloxacin free base starting material in water at room temperature and pH of about 7 was determined to be 73.3 μg/ml while that of the new amorphous besifloxacin free base (of Example 2) was 515.7 μg/ml.

Preparation of Solid Besifloxacin Free Base

TABLE 1

X-Ray Diffraction Peak Table for Besifloxacin Free Base Starting Material of Example 1

| Order of Peak | 2-Theta (degrees) | d (Å) | Relative Intensity (%) |
|---|---|---|---|
| 1 | 10.6 | 8.36 | 24.4 |
| 2 | 12.2 | 7.25 | 21 |
| 3 | 13.8 | 6.42 | 14.5 |
| 4 | 15 | 5.91 | 25 |
| 5 | 15.9 | 5.58 | 12.9 |
| 6 | 16.7 | 5.30 | 7.8 |
| 7 | 17.9 | 4.94 | 11.5 |
| 8 | 19.1 | 4.65 | 5.8 |
| 9 | 19.7 | 4.50 | 25.3 |
| 10 | 21.1 | 4.21 | 100 |
| 11 | 22 | 4.03 | 62.1 |
| 12 | 23.2 | 3.84 | 6.6 |
| 13 | 23.9 | 3.71 | 11.3 |
| 14 | 24.7 | 3.60 | 4.2 |
| 15 | 25.5 | 3.49 | 23.8 |
| 16 | 25.9 | 3.43 | 26 |
| 17 | 27.4 | 3.25 | 12.7 |
| 18 | 28.2 | 3.16 | 5.1 |
| 19 | 29.6 | 3.02 | 20.5 |
| 20 | 31.8 | 2.81 | 22.5 |
| 21 | 32.4 | 2.76 | 7.4 |
| 22 | 34.2 | 2.62 | 3.6 |
| 23 | 35.1 | 2.56 | 7.3 |

TABLE 2

X-Ray Diffraction Peak Table for Amorphous Besifloxacin Free Base of Example 2

| Order of Peak | 2-Theta (degrees) | d (Å) | Rel. Int. (%) |
|---|---|---|---|
| 1 | 7.06 | 12.51 | 100 |
| 2 | 9.40 | 9.40 | 44.5 |
| 3 | 10.66 | 8.29 | 25.6 |
| 4 | 13.70 | 6.46 | 40.9 |
| 5 | 18.72 | 7.74 | 40.9 |
| 6 (Halo) | 11-30 | NA | NA |

TABLE 3

X-Ray Diffraction Peak Table for an Amorphous Besifloxacin Free Base Prepared According to Example 3

| Order of Peak | 2-Theta (degrees) | d (Å) | Rel. Int. (%) |
|---|---|---|---|
| 1 | 6.92 | 12.76 | 100 |
| 2 | 8.18 | 10.80 | 45.7 |
| 3 | 9.44 | 9.36 | 13.8 |
| 4 | 10.64 | 8.31 | 14.9 |
| 5 | 13.40 | 6.60 | 47.9 |
| 6 | 19.00 | 4.67 | 9.2 |
| 7 (Halo) | 11-30 | NA | NA |

In another aspect, the present invention provides a pharmaceutical composition comprising an amorphous besifloxacin ((R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid) characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°.

In another aspect, the present invention provides a pharmaceutical composition comprising an amorphous besifloxacin ((R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid) characterized by a DSC (differential scanning calorimetry) melting peak at about 267-272° C.

In still another aspect, the present invention provides a pharmaceutical composition comprising an amorphous besifloxacin ((R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid) characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°, and a DSC (differential scanning calorimetry) melting peak at about 267-272° C.

In a further aspect, a pharmaceutical of the present invention comprises a solution comprising an amorphous besifloxacin free base as disclosed herein and a pharmaceutically acceptable carrier. In one embodiment, the pharmaceutically acceptable carrier comprises an aqueous medium. In another embodiment, such pharmaceutically acceptable carrier is a pharmaceutically acceptable aqueous buffer.

A pharmaceutical composition of the present invention can be used to treat infection, such as bacterial infection, by administering such a composition to a subject.

Such a pharmaceutical composition may be adapted for administration by appropriate routes, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a besifloxacin prepared according to the present invention with one or more carriers or excipients.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example skin, the compositions may be applied as a topical solution, suspension, emulsion, dispersion, ointment, or cream, as appropriate. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous medium.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 10 to 500 microns which is administered in the manner in which snuff is taken; i.e., by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers, or insufflators.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets.

Preferred unit dosage compositions are those containing a daily dose or sub-dose, as hereinabove recited, or an appropriate fraction thereof, of an active ingredient.

In one embodiment, such a pharmaceutical composition comprises an aqueous carrier.

In another embodiment, such a pharmaceutical composition comprises an organic carrier, such as a hydrophobic or a hydrophilic organic material.

A suitable concentration of the amorphous besifloxacin free base is in the range from about 0.001 to about 10 percent (or alternatively, from about 0.01 to about 5 percent, or from about 0.01 to about 2 percent, or from about 0.01 to about 1 percent, or from about 0.001 to about 1 percent, or from about 0.05 to about 1 percent, or from about 0.05 to about 2 percent, or from about 0.1 to about 0.5 percent, from about 0.5 to about 1 percent, from about 1 to about 2 percent) by weight of the total composition is believed adequately to provide therapeutic value for combating infection, such as bacterial infection caused by Gram-positive, Gram-negative bacteria or both.

In one embodiment, a composition of the present invention is in a form of a suspension or dispersion. In another embodiment, the suspension or dispersion is based on an aqueous solution. For example, a composition of the present invention can comprise micrometer- or nanometer-sized particles of the active ingredient suspended or dispersed in sterile saline solution. In another embodiment, the suspension or dispersion is based on a hydrophobic medium. For example, the micrometer- or nanometer-sized (such as in the range from about 0.1 to about 10 μm) particles of the active ingredient (or a salt or ester thereof) can be suspended in a hydrophobic solvent e.g., silicone oil, mineral oil, or any other suitable nonaqueous medium for delivery to the eye. In still another embodiment, the micrometer- or nanometer-sized particles of the active ingredient (or a salt or ester thereof) can be coated with a physiologically acceptable surfactant (non-limiting examples are disclosed below), then the coated particles are dispersed in a liquid medium. The coating can keep the particles in a suspension. Such a liquid medium can be selected to produce a sustained-release suspension. For example, the liquid medium can be one that is sparingly soluble in the ocular environment into which the suspension is administered. In still another embodiment, the active ingredient (or a salt or ester thereof) is suspended or dispersed in a hydrophobic medium, such as an oil. In still another embodiment, such a medium comprises an emulsion of a hydrophobic material and water. In still another embodiment, the insoluble active ingredient (or a salt or ester thereof) disclosed herein can be dosed by any normal drug delivery vehicle including but not limited to suspension in a liposome composition (both within and outside the liposome wall or strictly outside the liposome core), in the continuous phase of an emulsion or microemulsion, in the oil phase of the emulsion, or in a micellar solution using either charged or uncharged surfactants. A micellar solution wherein the surfactant is both the micelle forming agent and the anion of the active ingredient (or a salt or ester thereof) disclosed herein would be preferable.

In another aspect, a composition of the present invention can further comprise a non-ionic surfactant, such as polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). Such compounds are delineated in Martindale, $34^{th}$ ed., pp. 1411-1416 (Martindale, "The Complete Drug Reference," S. C. Sweetman (Ed.), Pharmaceutical Press, London, 2005) and in Remington, "The Science and Practice of Pharmacy," $21^{st}$ Ed., p. 291 and the contents of chapter 22, Lippincott Williams & Wilkins, New York, 2006). The concentration of a non-ionic surfactant, when present, in a composition of the present invention can be in the range from about 0.001 to about 5 weight percent (or alternatively, from about 0.01 to about 4, or from about 0.01 to about 2, or from about 0.01 to about 1, or from about 0.01 to about 0.5 weight percent). Any of these surfactants also can be used to coat micrometer- or nanometer-sized particles, as disclosed above.

In addition, a composition of the present invention can include one or more additives such as buffers, diluents, carriers, adjuvants, or other excipients. Any pharmacologically acceptable buffer suitable for application to the eye may be used. Other agents may be employed in the composition for a variety of purposes. For example, buffering agents, preservatives, co-solvents, oils, humectants, emollients, stabilizers, or antioxidants may be employed.

Water-soluble preservatives which may be employed include sodium bisulfite, sodium bisulfate, sodium thiosulfate, benzalkonium chloride, chlorobutanol, thimerosal, ethyl alcohol, methylparaben, polyvinyl alcohol, benzyl alcohol, phenylethyl alcohol, peroxide (such as hydrogen peroxide, urea hydrogen peroxide, or a source that generate a peroxide compound such as perborate), biguanide compounds, and quaternium compounds (such as polyquat-1, polyquat-10, etc.). These agents may be present in individual amounts of from about 0.001 to about 5 percent by weight (preferably, about 0.01 to about 2 percent by weight).

Suitable water-soluble buffering agents that may be employed are sodium carbonate, sodium borate, sodium phosphate, sodium acetate, sodium bicarbonate, etc., as approved by the United States Food and Drug Administration ("US FDA") for the desired route of administration. These agents may be present in amounts sufficient to maintain a pH of the system of between about 5 and about 8. As such, the buffering agent may be as much as about 5 percent on a weight to weight basis of the total composition. Electrolytes such as, but not limited to, sodium chloride and potassium chloride may also be included in the composition. Physiologically acceptable buffers include, but are not limited to, a phosphate buffer or a Tris-HCl buffer (comprising tris(hydroxymethyl)aminomethane and HCl). For example, a Tris-HCl buffer having pH of 7.4 comprises 3 g/l of tris(hydroxymethyl)aminomethane and 0.76 g/l of HCl. In yet another aspect, the buffer is 10× phosphate buffer saline ("PBS") or 5× PBS solution.

Other buffers also may be found suitable or desirable in some circumstances, such as buffers based on HEPES (N-{2-hydroxyethyl}piperazine-N'-{2-ethanesulfonic acid}) having $pK_a$ of 7.5 at 25° C. and pH in the range of about 6.8-8.2; BES (N,N-bis{2-hydroxyethyl}2-aminoethanesulfonic acid) having $pK_a$ of 7.1 at 25° C. and pH in the range of about 6.4-7.8; MOPS (3-{N-morpholino}propanesulfonic acid) having $pK_a$ of 7.2 at 25° C. and pH in the range of about 6.5-7.9; TES (N-tris{hydroxymethyl}-methyl-2-aminoethanesulfonic acid) having $pK_a$ of 7.4 at 25° C. and pH in the range of about 6.8-8.2; MOBS (4-{N-morpholino}butanesulfonic acid) having $pK_a$ of 7.6 at 25° C. and pH in the range of about 6.9-8.3; DIPSO (3-(N,N-bis{2-hydroxyethyl}amino)-2-hydroxypropane)) having $pK_a$ of 7.52 at 25° C. and pH in the range of about 7-8.2; TAPSO (2-hydroxy-3{tris(hydroxymethyl)methylamino}-1-propanesulfonic acid)) having $pK_a$ of 7.61 at 25° C. and pH in the range of about 7-8.2; TAPS ({(2-hydroxy-1,1-bis(hydroxymethyl)ethyl)amino}-1-propanesulfonic acid)) having $pK_a$ of 8.4 at 25° C. and pH in the range of about 7.7-9.1; TABS (N-tris(hydroxymethyl)methyl-4-aminobutanesulfonic acid) having $pK_a$ of 8.9 at 25° C. and pH in the range of about 8.2-9.6; AMPSO (N-(1,1-dimethyl-2-hydroxyethyl)-3-amino-2-hydroxypropanesulfonic acid)) having $pK_a$ of 9.0 at 25° C. and pH in the range of about 8.3-9.7; CHES (2-cyclohexylamino)ethanesulfonic acid) having $pK_a$ of 9.5 at 25° C. and pH in the range of about 8.6-10.0; CAPSO (3-(cyclohexylamino)-2-hydroxy-1-propanesulfonic acid) having $pK_a$ of 9.6 at 25° C. and pH in the range of about 8.9-10.3; or CAPS (3-(cyclohexylamino)-1-propane sulfonic acid) having $pK_a$ of 10.4 at 25° C. and pH in the range of about 9.7-11.1.

In one aspect, the composition has a pH that is suitable for administration into a subject; e.g., to render the composition non-irritating. For example, for topical ophthalmic administration, a desired pH is in the range from about 5 to about 8 (or alternatively from about 6 to about 7, or from about 6.4 to about 6.8).

In one aspect, the composition has a pH of about 7. Alternatively, the composition has a pH in a range from about 7 to about 7.5.

In another aspect, the composition has a pH of about 7.4.

In yet another aspect, a composition also can comprise a viscosity-modifying compound designed to facilitate the administration of the composition into the subject or to promote the bioavailability in the subject. In still another aspect, the viscosity-modifying compound may be chosen so that the composition is not readily dispersed after being administered into an ocular environment (such as the ocular surface, conjunctiva, or vitreous). Such compounds may enhance the viscosity of the composition, and include, but are not limited to: monomeric polyols, such as, glycerol, propylene glycol, ethylene glycol; polymeric polyols, such as, polyethylene glycol; various polymers of the cellulose family, such as hydroxypropylmethyl cellulose ("HPMC"), carboxymethyl cellulose ("CMC") sodium, hydroxypropyl cellulose ("HPC"); polysaccharides, such as hyaluronic acid and its salts, chondroitin sulfate and its salts, dextrans, such as, dextran 70; water soluble proteins, such as gelatin; vinyl polymers, such as, polyvinyl alcohol, polyvinylpyrrolidone, povidone; carbomers, such as carbomer 934P, carbomer 941, carbomer 940, or carbomer 974P; and acrylic acid polymers. In general, a desired viscosity can be in the range from about 1 to about 400 centipoises ("cp" or mPa.s).

In another aspect, the present invention provides a method for producing a composition comprising amorphous besifloxacin free base (or a salt or ester thereof), the method comprising: (a) providing said amorphous besifloxacin free base (or a salt or ester thereof); and (b) dispersing an amount of said amorphous besifloxacin free base (or a salt or ester thereof) in a sufficient amount of said medium to produce said composition to achieve a predetermined concentration of said amorphous besifloxacin free base (or a salt or ester thereof) in said medium. Alternatively, a portion of amorphous besifloxacin free base (or a salt or ester thereof) remains in a solid phase for a period longer than 2 days, or 1 week, or 1 month, or 2 months, or 3 months, or 4 months, or 5 months, or 6 months, or 1 year, or 2 years after said amorphous besifloxacin free base (or a salt or ester thereof) has been in contact with said medium. In one embodiment, the method can optionally include a step of reducing the size of amorphous besifloxacin free base (or a salt or ester thereof) before dispersing such besifloxacin (or a salt or ester thereof) in the medium.

In still another aspect, the present invention provides a method for producing an amorphous besifloxacin free base. The method comprises: (a) preparing a saturated solution of besifloxacin free base in benzyl alcohol at a first temperature in the range from about 80 to about 140° C.; (b) reducing the temperature of the solution to a second temperature in the range from about −10 to about 25° C.; (c) holding the solution at said second temperature for 10 minutes to 4 weeks, whereby said amorphous besifloxacin solid is formed.

In a further aspect, the process further comprises: (d) recovering said amorphous besifloxacin solid from said solution; and (e) removing benzyl alcohol from said amorphous besifloxacin solid.

In one embodiment, said removing is carried out at subatmospheric pressure at a temperature from about room temperature to about 50° C.

In another embodiment, a process for preparing an amorphous besifloxacin solid comprises: (a) preparing a first saturated solution of besifloxacin free base in benzyl alcohol at a first temperature in the range form about 60 to about 180° C.; (b) reducing the temperature of the solution to a second temperature in the range from about −10 to about 40° C.; (c) preparing a second saturated solution of besifloxacin free base in a second organic solvent other than benzyl alcohol at said second temperature, said second organic solvent being soluble in benzyl alcohol at said second temperature; (d) adding an amount of said second saturated solution to said first saturated solution at said second temperature to form a mixture; and (e) holding said mixture at said second temperature for a time from about 10 minutes to about 4 weeks, whereby said amorphous besifloxacin solid is formed.

In a further aspect, the process further comprises: (f) recovering said amorphous besifloxacin solid from said solution; and (g) removing benzyl alcohol and said second organic solvent from said amorphous besifloxacin solid.

In one embodiment, said removing is carried out at subatmospheric pressure at a temperature from about room temperature to about 50° C.

In still another embodiment, a process for preparing an amorphous besifloxacin solid comprises: (a) preparing a first saturated solution of besifloxacin free base in benzyl alcohol at a first temperature in the range form about 60 to about 180° C.; (b) reducing the temperature of the solution to a second temperature in the range from about −10 to about 40° C.; (c) preparing a second saturated solution of besifloxacin free base in a second organic solvent other than benzyl alcohol at said second temperature, said second organic solvent being soluble in benzyl alcohol at said second temperature; (d) adding an amount of said second saturated solution to said first saturated solution at said second temperature to form a mixture; (e) holding said mixture at said second temperature for a time from about 10 minutes to about 4 weeks, whereby said amorphous besifloxacin solid is formed; and (f) repeating step (e) at least more time.

In still another embodiment, a process for preparing an amorphous besifloxacin solid comprises: (a) preparing a first saturated solution of besifloxacin free base in benzyl alcohol at a first temperature in the range form about 60 to about 180° C.; (b) reducing the temperature of the solution to a second temperature in the range from about −10 to about 40° C.; (c) preparing a second saturated solution of besifloxacin free base in a second organic solvent other than benzyl alcohol at said second temperature, said second organic solvent being soluble in benzyl alcohol at said second temperature; (d) adding an amount of said second saturated solution to said first saturated solution at said second temperature to form a mixture; (e) holding said mixture at said second temperature for a time from about 10 minutes to about 4 weeks, whereby said amorphous besifloxacin solid is formed; (f) repeating step (e) at least more time; (g) recovering said amorphous besifloxacin solid from said solution; and (h) removing benzyl alcohol and said second organic solvent from said amorphous besifloxacin solid.

The method can further comprise subjecting the recovered amorphous besifloxacin free base to a step of size reduction to nanometer- or micrometer-sized particles.

Some compositions of the present invention are disclosed in the examples below. It should be understood that the proportions of the listed ingredients may be adjusted for specific circumstances.

EXAMPLE 4

TABLE 4

| Ingredient | Amount |
| --- | --- |
| Carbopol 934P NF | 1 g |
| Propylene glycol | 5 g |
| EDTA | 0.1 mg |
| Amorphous besifloxacin free base | 0.6 g |
| Purified water | q.s. to 100 g |

TABLE 4-continued

An appropriate proportion of EDTA (e.g., shown in Table 14) is added to purified water in a stainless steel jacketed vessel that is equipped with a stirring mechanism. An appropriate amount of carbopol 934P NF is added, over a period of five to ten minutes to form a substantially uniform dispersion. Propylene glycol is added to the resulting mixture while mixing for three to ten minutes. Then, an appropriate amount to amorphous besifloxacin free base prepared according to a method disclosed hereinabove, which may be previously micronized, is added to the contents of the vessel over a period of three to five minutes while mixing continues until the compound is substantially dispersed. The pH of the mixture is adjusted to 6.4-6.7 using 1 N NaOH. The final composition is sterilized, using, for example, heat or radiation and then packaged in appropriate containers.

EXAMPLE 5

A procedure similar to that disclosed in Example 4 is used to produce the composition of the present invention having the ingredients listed in Table 5.

TABLE 5

| Ingredient | Amount (% by weight, except where "ppm" is indicated) |
| --- | --- |
| Povidone | 1.5 |
| HAP (30%) | 0.05 |
| Glycerin | 3 |
| Propylene glycol | 3 |
| Hydrochloric acid addition salt of amorphous besifloxacin free base | 0.7 |
| Alexidine 2HCl | 1-2 ppm |
| Purified water | q.s. to 100 |

Note: "HAP" denotes hydroxyalkyl phosphonates, such as those known under the trade name Dequest®. HAPs can be used as chelating agents and have been shown to inhibit bacterial and fungal cell replication.

EXAMPLE 6

A procedure similar to that disclosed in Example 4 is used to produce the composition of the present invention having the ingredients listed in Table 6.

TABLE 6

| Ingredient | Amount (% by weight, except where "ppm" is indicated) |
| --- | --- |
| Glycerin | 3 |
| Propylene glycol | 3 |
| Amorphous besifloxacin free base | 0.4 |
| Polyquat-1 | 1-10 ppm |
| Sunflower oil | q.s. to 100 |

EXAMPLE 7

A modification of the procedure disclosed in Example 4 is used to produce the composition of the present invention having the ingredients listed in Table 7.

An appropriate proportion of polysorbate 80 (e.g., shown in Table 4) is added to approximately 20 percent of the desired final volume of purified water in a stainless steel jacketed vessel that is equipped with a stirring mechanism. Glycerin and propylene glycol are then added to the mixture while mixing continues for five more minutes. To a sterilized second vessel, heated to about 80° C. and equipped with a stirring mechanism, containing approximately 70 percent of the desired final volume of purified water, an appropriate amount of CMC-MV is added over a period of three to five minutes while mixing continues until the CMC forms a substantially uniform solution. The contents of the second vessel are cooled to about room temperature and then the contents of the first vessel are transferred into the second vessel. The remaining of the desired volume of purified water is added to the second vessel. Then, an appropriate amount of amorphous besifloxacin free base and a second anti-infective drug (such as ciprofloxacin) are added to the contents of the second vessel over a period of three to five minutes while mixing continues until the drugs are substantially uniformly dispersed. The pH of the mixture is adjusted to 6.5-6.7 using 1 N NaOH. The final composition is sterilized, using, for example, heat or radiation, and packaged in appropriate containers.

TABLE 7

| Ingredient | Amount (% by weight, except where "ppm" is indicated) |
| --- | --- |
| Carboxymethyl cellulose, medium viscosity ("CMC-MV") | 0.5 |
| Glycerin | 3 |
| Propylene glycol | 3 |
| Amorphous besifloxacin free base microparticles | 0.6 |
| Cirpofloxacin microparticles | 0.2 |
| Polysorbate 80 ® (a surfactant) | 0.25 |
| Stabilized oxychloro complex | 20-50 ppm |
| Purified water | q.s. to 100 |

EXAMPLE 8

A procedure similar to that of Example 4 is used to produce a composition comprising the ingredients listed in Table 8.

TABLE 8

| Ingredient | Amount (% by weight, except where "ppm" is indicated) |
| --- | --- |
| Glycerin | 3 |
| Propylene glycol | 3 |
| Amorphous besifloxacin free base microparticles | 0.5 |
| Tween ® 80 | 0.25 |
| Alexidine | 1-2 ppm |
| Corn oil | q.s. to 100 |

EXAMPLE 9

A procedure similar to that of Example 7 is used to produce a composition comprising the ingredients listed in Table 9.

TABLE 9

| Ingredient | Amount (% by weight, except where "ppm" is indicated) |
| --- | --- |
| CMC (MV) | 0.5 |
| Glycerin | 3 |
| Propylene glycol | 3 |
| Amorphous besifloxacin free base microparticles | 0.75 |
| Moxifloxacin microparticles | 0.25 |
| Tyloxapol (a surfactant) | 0.25 |
| Alexidine 2HCl | 1-2 ppm |
| Purified water | q.s. to 100 |

EXAMPLE 10

A procedure similar to that of Example 4 is used to produce a composition comprising the ingredients listed in Table 10.

TABLE 10

| Ingredient | Amount (% by weight, except where "ppm" is indicated) |
| --- | --- |
| HPMC | 0.5 |
| Glycerin | 3 |
| Propylene glycol | 3 |
| Amorphous besifloxacin free base microparticles | 0.5 |
| Gatifloxacin microparticles | 0.2 |
| Azithromycin microparticles | 0.2 |
| Tyloxapol (a surfactant) | 0.25 |
| Benzalkonium chloride | 100 ppm |
| Purified water | q.s. to 100 |

Alternatively, purified water may be substituted with an oil, such as fish-liver oil, peanut oil, sesame oil, coconut oil, sunflower oil, corn oil, or olive oil to produce an oil-based composition comprising besifloxacin molecular crystal.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. An amorphous solid-state form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°.

2. An amorphous solid-state form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by a DSC (differential scanning calorimetry) melting peak at about 267-272° C.

3. The amorphous solid-state form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid of claim 2, wherein the amorphous solid-state form is further characterized by a DSC (differential scanning calorimetry) melting peak at about 267-272° C.

4. A process for preparing an amorphous besifloxacin solid comprising: (a) preparing a first saturated solution of besifloxacin free base in benzyl alcohol at a first temperature in the range from about 60 to about 180° C.; (b) reducing the temperature of the solution to a second temperature in the range from about −10 to about 40° C.; (c) preparing a second saturated solution of besifloxacin free base in a second organic solvent other than benzyl alcohol at said second temperature, said second organic solvent being soluble in benzyl alcohol at said second temperature; (d) adding an amount of said second saturated solution to said first saturated solution at said second temperature to form a mixture; and (e) holding said mixture at said second temperature for a time from about 10 minutes to about 4 weeks, whereby said amorphous besifloxacin solid is formed.

5. The process of claim 4, wherein said amorphous besifloxacin free base is characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°.

6. The process of claim 4, further comprising: (f) recovering said amorphous besifloxacin solid from said solution; and (g) removing benzyl alcohol and said second organic solvent from said amorphous besifloxacin solid.

7. The process of claim 4, wherein said amorphous besifloxacin free base is characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°, and a DSC (differential scanning calorimetry) melting peak at about 267-272° C.

8. The process of claim 6, wherein said removing is carried out at subatmospheric pressure at a temperature from about room temperature to about 50° C.

9. A process for preparing an amorphous besifloxacin solid comprising: (a) preparing a first saturated solution of besifloxacin free base in benzyl alcohol at a first temperature in the range from about 80 to about 140° C.; (b) reducing the temperature of the solution to a second temperature in the range from about −10 to about 25° C.; (c) holding the solution at said second temperature for 10 minutes to 4 weeks, whereby said amorphous besifloxacin solid is formed.

10. The process of claim 9, wherein said amorphous besifloxacin free base is characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°.

11. The process of claim 10, further comprising repeating step (e) at least more time.

12. The process of claim 10, wherein said amorphous besifloxacin free base is characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°, and a DSC (differential scanning calorimetry) melting peak at about 267-272° C.

13. A process for preparing an amorphous besifloxacin solid comprising: (a) preparing a first saturated solution of besifloxacin free base in benzyl alcohol at a first temperature in the range from about 60 to about 180° C.; (b) reducing the temperature of the solution to a second temperature in the range from about −10 to about 40° C.; (c) preparing a second saturated solution of besifloxacin free base in a second organic solvent other than benzyl alcohol at said second temperature, said second organic solvent being soluble in benzyl alcohol at said second temperature; (d) adding an amount of said second saturated solution to said first saturated solution at said second temperature to form a mixture; (e) holding said mixture at said second temperature for a time from about 10 minutes to about 4 weeks, whereby said amorphous besifloxacin solid is formed; (f) repeating step (e) at least more time; (g) recovering said amorphous besifloxacin solid from said solution; and (h) removing benzyl alcohol and said second organic solvent from said amorphous besifloxacin solid.

14. The process of claim 13, wherein said amorphous besifloxacin free base is characterized by an X-ray powder diffraction ("XRPD") spectrum that comprises peaks at 2θ angles of 6.9-7.1, 9.4, 10.6-10.7, and 13.4-13.7°±0.2°, and a diffuse halo pattern at 11-30°, and a DSC (differential scanning calorimetry) melting peak at about 267-272° C.

* * * * *